US00PP36247P2

(12) United States Plant Patent
Holtmaat

(10) Patent No.: US PP36,247 P2
(45) Date of Patent: Nov. 5, 2024

(54) ***SILENE* PLANT NAMED 'Sil005'**

(50) Latin Name: *Silene virginica*
Varietal Denomination: Sil005

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 18/585,368

(22) Filed: Feb. 23, 2024

(51) Int. Cl.
*A01H 5/02* (2018.01)
*A01H 6/30* (2018.01)

(52) U.S. Cl.
USPC ..... Plt./481
CPC ..... *A01H 6/30* (2018.05)

(58) Field of Classification Search
USPC ..... Plt./481
CPC ..... A01H 6/30; A01H 5/02
See application file for complete search history.

*Primary Examiner* — Keith O. Robinson
(74) *Attorney, Agent, or Firm* — Penny J. Aguirre

(57) ABSTRACT

A new cultivar of *Silene* plant named 'Sil005' that is characterized by its tall plant height, its abundant shoot production, its foliage that is dark green in color, and its very floriferous blooming habit.

3 Drawing Sheets

Botanical classification: *Silene virginica.*
Variety denomination: 'Sil005'.

BACKGROUND OF THE INVENTION

The present invention relates to a new and distinct cultivar of *Silene virginica* and will be referred to hereafter by its cultivar name 'Sil005'. 'Sil005' represents a new perennial grown for landscape and container use.

The Inventor discovered the new cultivar in June of 2022 as a young potted plant that derived from tissue culture of 'Jackson Valentine' in Heerhugowaard, The Netherlands, and therefore assumed to be a naturally occurring chimeral mutation of *Silene* 'Jackson Valentine' (not patented).

Asexual propagation of the new cultivar was first accomplished by tissue culture using meristematic tissue under the direction of the Inventor in Heerhugowaard, The Netherlands in August of 2022. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Sil005' as a unique cultivar of *Silene.*

1. 'Sil005' exhibits a tall plant height.
2. 'Sil005' exhibits abundant shoot production.
3. 'Sil005' exhibits foliage that is dark green in color.
4. 'Sil005' exhibits a very floriferous blooming habit.

The female parent of 'Sil005' differs from 'Sil005' in having a shorter plant height, less production of shoots, leaves that are lighter green in color, and a less floriferous blooming habit. 'Sil005' can be most closely compared to *Silene* 'Fire Pink' (not patented). 'Fire Pink' is similar to 'Sil005' in flower color. 'Fire Pink' differs from 'Sil005' in having weaker stems, a shorter plant height, leaves that are lighter green in color, and a much less floriferous blooming habit.

BRIEF DESCRIPTION OF THE DRAWINGS

The accompanying color photographs illustrate the overall appearance and distinct characteristics of the new *Silene*. The photographs were taken of a 15-month-old plant of 'Sil005' as grown in a 19-cm container in an unheated greenhouse in Heerhugowaard, The Netherlands.

The photograph in FIG. 1 provides a side view of a plant 'Sil005' in bloom.

Figure 1:
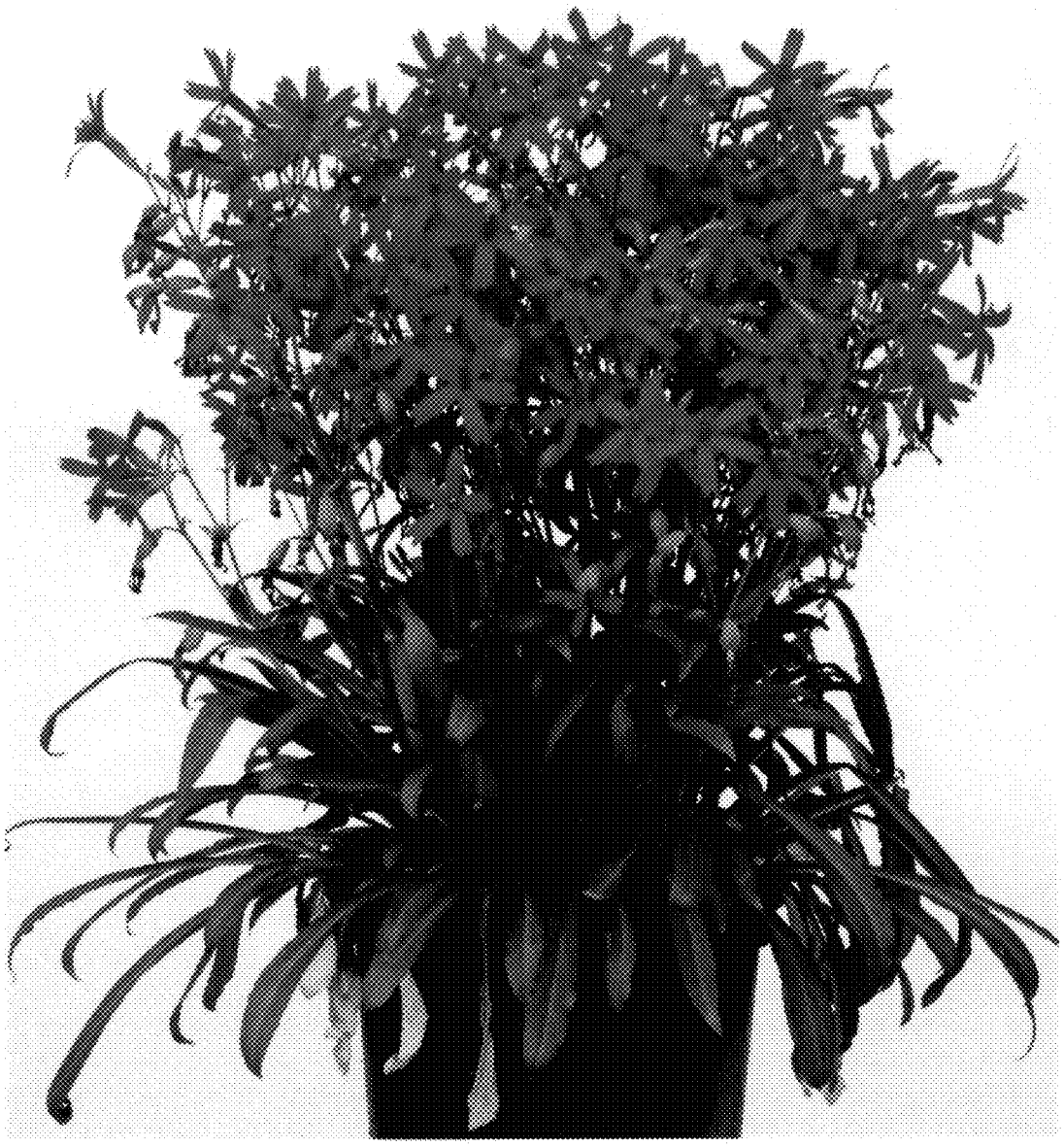
Figure 2:
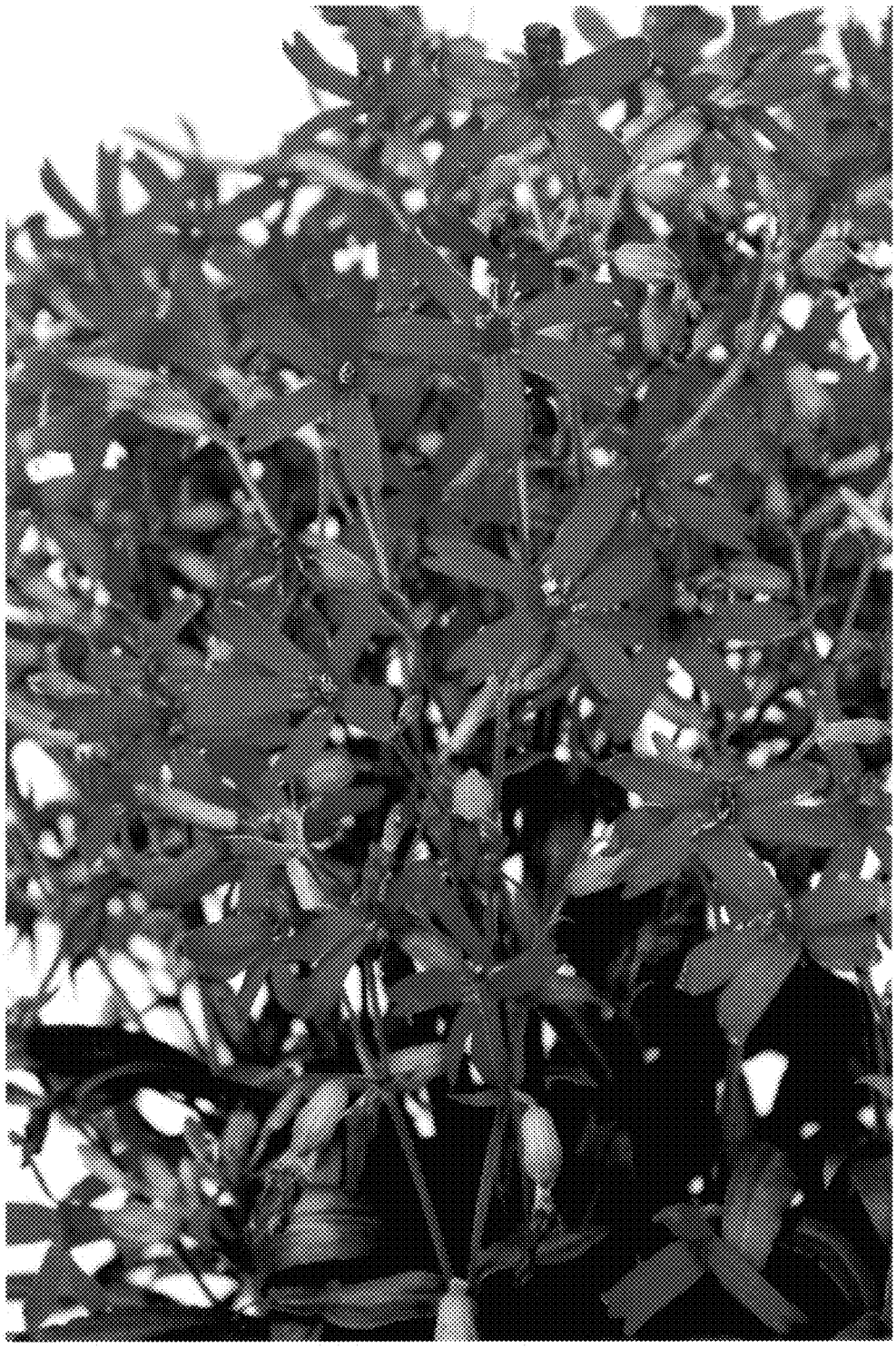

The photograph in FIG. 2 provides a close-up view of the flowers of 'Sil005'.

Figure 3:
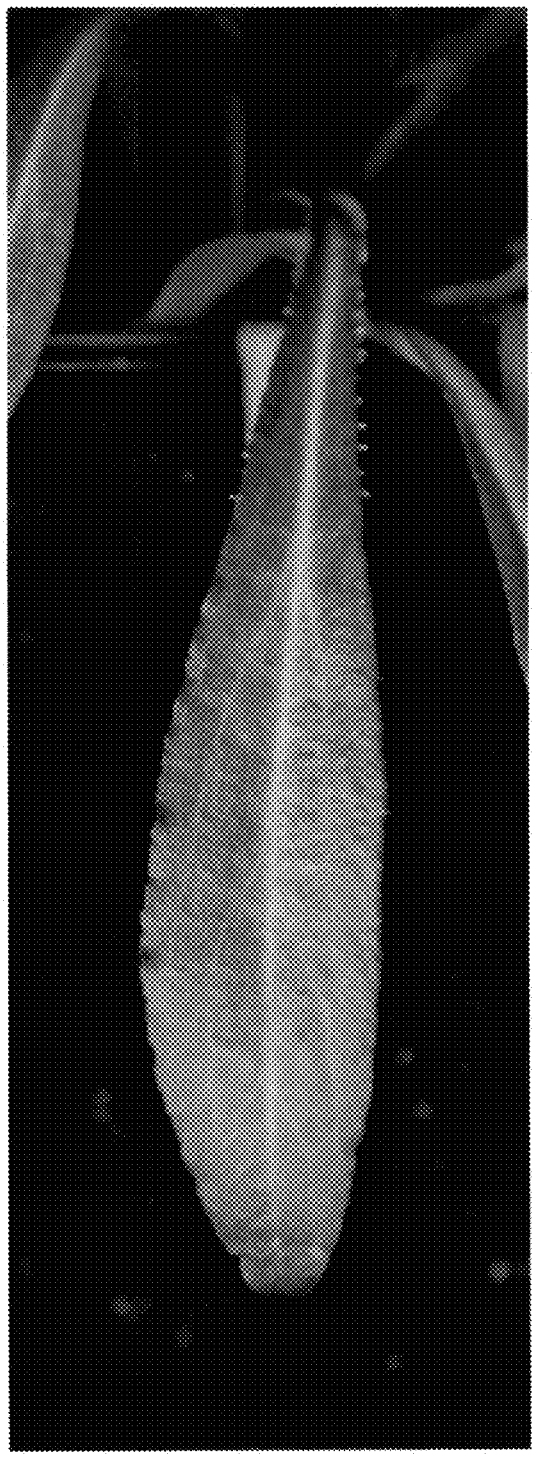

The photograph in FIG. 3 provides a close-up view of a leaf of 'Sil005'.

The colors in the photographs are as close as possible with the digital photography techniques available, the color values cited in the detailed botanical description accurately describe the colors of the new *Silene.*

DETAILED BOTANICAL DESCRIPTION

The following is a detailed description of 15-month-old plants of 'Sil005' as grown in 19-cm containers in an unheated greenhouse in Heerhugowaard, Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—8 weeks, late April to late June in The Netherlands.

*Plant type.*—Herbaceous perennial.

*Plant habit.*—Broadly upright.

*Height and spread*.—An average of 21 cm (top of foliage plane), 38 cm (top of floral plane) and 43 cm in spread as a 15-month-old plant grown in a container, reaches an average of 50 cm in height and spread when grown in the landscape.

*Hardiness*.—At least in U.S.D.A. Zones 5 to 10.

*Diseases and pests*.—No susceptibility or resistance to pests and diseases has been observed.

*Root description*.—Fibrous.

*Propagation*.—Tissue culture.

*Time required for root initiation*.—Roots initiate in 3 weeks, a rooted cutting is produced in 10 weeks.

*Growth rate*.—Moderate.

Stem description:

*Shape*.—Round.

*Stem color*.—Young; upper surface (sun) darker than 152A, lower surface (shaded) a blend of 152A and N200A, mature; upper surface (sun)146A, lower surface (shaded) 147A, internodes; 147A, strongly tinged with N199B.

*Stem size*.—Average of 12 cm in length and 4.5 mm in diameter.

*Stem surface*.—Very slightly glossy, densely covered with short, slightly sticky hairs, up to 1 mm in length, NN155D in color.

*Stem strength*.—Strong.

*Stem aspect*.—Held in an average angle of 77.5° (varying between 65° and 90°).

*Internode length*.—8.2 cm.

*Branching*.—Basal branches only, an average of 34 branches per plant.

Foliage description:

*Leaf size*.—Whole leaves; average of 23.1 cm in length and 1.9 cm in width, stem leaves; 6.1 cm in length and 1.3 cm in width.

*Leaf quantity*.—Average of 4 per branch (2 pairs).

*Leaf shape*.—Ovate.

*Leaf division*.—Simple.

*Leaf base*.—Cuneate, decurrent.

*Leaf apex*.—Acute, pointed downward to curled downward.

*Leaf venation*.—Pinnate, upper surface color; 146D, proximal end N186D, lower surface color; 146D, proximal end 183A.

*Leaf margins*.—Finely serrate, slightly undulate, unlobed.

*Leaf attachment*.—Sessile.

*Leaf arrangement*.—Opposite.

*Leaf surface*.—Both surfaces are smooth and glabrous, very slightly glossy, non-rugose, no pubescence present on lamina, lower $2/3^{rd}$ to lower half of margins moderately covered with short hairs and more densely towards the proximal end with hairs 1 mm in length and NN155D in color.

*Leaf color*.—Young upper surface; 143A, young lower surface; 138B, mature upper surface; NN137B, proximal end a blend of 183A and N186D, mature lower surface; 147B and 191A, proximal end a blend of 183A and N186D.

Flower description:

*Inflorescence type*.—Compound cyme.

*Inflorescence size*.—Average of 23 cm in height and 17.3 cm in diameter.

*Fragrance*.—None.

*Lastingness*.—Up to 14 days, self-cleaning, persistent.

*Flower quantity*.—Average of 42 flowers per inflorescence, average of 1400 flowers and flower buds per plant.

*Flower size*.—4.2 cm in diameter, 3.2 cm in depth, throat; 3.2 cm in depth, 4 mm in diameter, tube; 2 cm in length, 5 mm in diameter.

*Flower buds*.—Average of 1.2 cm in length, 3 mm in diameter, color; lower half 146D, upper half 148A, axially veined 199A, narrowly elliptic in shape, surface is matte and moderately to densely covered with very short glandular hairs; slightly sticky, 0.3 mm in length, and too small to measure color.

*Flower petals*.—Rotate, average of 5 per flower, 1 whorl, un-fused, held in tube, 4 cm in length, 6 mm in width, oblanceolate in shape, apex emarginate to cleft, narrow cuneate base, entire margin, both surfaces are smooth, glabrous, slightly velvety, matte, lower half is moderately glossy, color: when opening and fully open upper surface; upper half 42A, bifid claw 48A, lower half 48A, base 145B, when opening lower surface; upper half a blend of 46C and 50A, lower half 51A, base 145B, when fully open lower surface; upper half 47B, lower half 46B, base 145B.

*Calyx*.—Campanulate, average of 1.6 cm in length and 6 mm in diameter.

*Sepals*.—5, rotate, fused into a campanulate tube, 1 whorl, 1.6 cm in length, 3 mm in width, oblanceolate in shape, acute apex, base is fused, margins entire, upper surface smooth, glabrous, slightly glossy, lower surface matte, moderately to densely covered with very short glandular hairs, slightly sticky, hairs up to 0.3 mm in length, too small to measure color, color: when opening upper surface; 148C, tinged 182C, veined 146B, when opening lower surface; 148D, tinged with 182C to 182D, veined 146C, when fully open upper surface; 148D, tinged 182C, veined 146B, when fully open lower surface 185D, veined 146B.

*Peduncles*.—Moderately strong, 7.2 cm in length and 3 mm in diameter, held in a vertical angle, secondary peduncles an average of 30° to main peduncle, color; 146A, lower side 147A, surface is smooth, densely covered with short slightly sticky hairs, 0.75 mm in length, NN155D in color, very slightly glossy.

*Pedicels*.—Moderately strong, 5 mm in length and 1 mm in diameter, held in a vertical angle, secondary pedicels an average of 30° to main peduncles, color; 147A, lower surface 176B, surface is smooth, densely covered with short slightly sticky hairs; 0.75 mm in length, NN155D in color, very slightly glossy.

*Bracts*.—2 bracts are present at each node of inflorescence, both surfaces 143A in color, narrow ovate to lanceolate in shape, 5 mm in length, 2 mm in width, acute apex, cuneate base, both surfaces and margins are moderately covered with very short glandular hairs, slightly sticky, 0.5 mm in length, and too small to measure color.

Reproductive organs:

*Gynoecium*.—Pistils; 3, average of 2.3 cm in length, stigma; pointed in shape, 2 mm in length and diameter, 56D in color, style; 2.27 cm in length, color in 54A, proximal end 155A, ovary; 144C in color.

*Androecium*.—Stamens; 10, filament; 2 cm in length, color is 54C, proximal end 155A, anther; basifixed, oblong in shape, 2 mm in length, 1 mm in width, 200B, pollen; low in quantity, 200C in color.

*Fruit and seed*.—No fruit or seeds have been observed.

It is claimed:

1. A new and distinct cultivar of *Silene* plant named 'Sil005' as herein illustrated and described.

* * * * *